United States Patent
Ikemoto et al.

(10) Patent No.: US 10,138,502 B2
(45) Date of Patent: Nov. 27, 2018

(54) METHOD FOR PRODUCING OIL CONTAINING POLYUNSATURATED FATTY ACID USING LIPASE

(71) Applicant: NIPPON SUISAN KAISHA, LTD., Chiyoda-ku, Tokyo (JP)

(72) Inventors: Hideo Ikemoto, Hachioji (JP); Nobushige Doisaki, Hachioji (JP); Yasuo Umehara, Hakodate (JP)

(73) Assignee: NIPPON SUISAN KAISHA, LTD., Tokyo (JP)

( * ) Notice: Subject to any disclaimer, the term of this patent is extended or adjusted under 35 U.S.C. 154(b) by 0 days.

(21) Appl. No.: 15/099,899

(22) Filed: Apr. 15, 2016

(65) Prior Publication Data

US 2016/0230199 A1 Aug. 11, 2016

Related U.S. Application Data

(63) Continuation of application No. 13/700,647, filed as application No. PCT/JP2011/062170 on May 27, 2011, now abandoned.

(30) Foreign Application Priority Data

May 28, 2010 (JP) .................... 2010-122688

(51) Int. Cl.
| | | |
|---|---|---|
| C12P 7/64 | (2006.01) | |
| A23D 9/04 | (2006.01) | |
| A23D 9/013 | (2006.01) | |
| C11B 3/00 | (2006.01) | |
| C11B 3/16 | (2006.01) | |
| C11C 1/04 | (2006.01) | |

(52) U.S. Cl.
CPC ............ *C12P 7/6472* (2013.01); *A23D 9/013* (2013.01); *A23D 9/04* (2013.01); *C11B 3/001* (2013.01); *C11B 3/003* (2013.01); *C11B 3/16* (2013.01); *C11C 1/045* (2013.01); *Y02E 50/17* (2013.01)

(58) Field of Classification Search
CPC ......... A23D 9/04; A23D 9/013; C12P 7/6472; C11B 3/001; C11B 3/003; C11B 3/16; C11C 1/045; Y02E 50/17
See application file for complete search history.

(56) References Cited

U.S. PATENT DOCUMENTS 5,945,318 A 8/1999 Breivik et al.
2009/0176284 A1 7/2009 Furihata et al.

FOREIGN PATENT DOCUMENTS

| CN | 101348807 A | 1/2009 |
|---|---|---|
| JP | S58165796 A | 9/1983 |
| JP | 1269496 A | 10/1989 |
| JP | 416519 A | 3/1992 |
| JP | 751075 A | 2/1995 |
| JP | 7268382 A | 10/1995 |
| JP | 8214892 A | 8/1996 |
| JP | 200154396 A | 2/2001 |
| WO | 9719601 A1 | 6/1997 |
| WO | 9818952 A1 | 5/1998 |
| WO | 2007119811 A1 | 10/2007 |
| WO | 2008093378 A1 | 8/2008 |
| WO | 2009017102 A1 | 2/2009 |

OTHER PUBLICATIONS

Lyberg A-N et al., "Lipase-catalysed enrichment of DHA and EPA in acylglycerols resulting from squid oil ethanolysis", Eur. J. Lipid Sci Technol., 2008, vol. 110, pp. 317-324.*
Adachi, Shuichi et al. "Acidolysis of Sardine Oil by Lipase to Concentrate Eicosapentaenoic and Docosahexaenoic Acids in Glycerides", J. Ferment. Bioeng., 1993, vol. 75, No. 4, p. 269-264.
Fajardo A. Ramirez, et al., "Concentration of Eicosapentaenoic Acid by Selective Esterification Using Lipases", J. Am. Oil Chem. Soc., 2006, vol. 83, No. 3, p. 215-221 (document unavailable).
Gross M. et al., Fish oil triglicerides Vs. ethyl esters, Phisician Recommended Nutriceuticals, May 11, 2004, pp. 1-2; published on the web at: http://pmomegahealth.com/wp-content/uploads/TGvsEE_English_04-05-11_review2.pdf.
International Search Report for International Application No. PCT/JP2011/062170, dated Jul. 12, 2011, with English translation.
Kazuaki Suzuki, "Concentration of Docosahexaenoic Acid by Lipase", Food Chemicals, 1998, vol. 14. No. 8, pp. 19-26 (document unavailable).
Mori, T.A. et al. Docosahexaen Acid but Not Eicosapentaenoic Acid Lowers Ambulatory Blood Pressure and Heart Rate in Humans, Hypertension, 1999, vol. 34, pp. 253-260.
U.S. Final Office Action corresponding to U.S. Appl. No. 13/700,647 dated Dec. 9, 2014.
U.S. Final Office Action corresponding to U.S. Appl. No. 13/700,647 dated Jan. 20, 2016.
U.S. Non Final Office Action corresponding to U.S. Appl. No. 13/700,647 dated Jun. 19, 2015.
Zambiazi R.C. et al. Fatty Acid Composition of Vegetable Oils and Fats, B.Ceppa, curitiba, Jan./Jun. 2007, vol. 25, No. 1, pp. 111-120.
Cerdan L.E. et al., Synthesis of Polyunsaturated Fatty Acid-Enriched Triglycerides by Lipase-Catalyzed Esterification, JAOCS, 1998 vol. 75, No. 10, pp. 1329-1337.
Moore S.R. et al., Production of triglycerides enriched in long-chain n-3 polyunsaturated fatty acids from fish oil, JAOCS, 1996, vol. 73, No. 11, pp. 1409-1414.
Tanaka Y. et al., "Concentration of Docosahexaenoic Acid in Glyceride by Hydrolysis of Fish Oil and Candida cyclindracea Lipase", JAOCS, Dec. 1992, vol. 69, No. 12, pp. 1210-1214.

(Continued)

*Primary Examiner* — Satyendra K Singh
(74) *Attorney, Agent, or Firm* — Cantor Colburn LLP

(57) ABSTRACT

A method for lowering saturated fatty acid content, the method comprising concentrating polyunsaturated fatty acid using a lipase having low reactivity for the polyunsaturated fatty acid to react with a glyceride containing a polyunsaturated fatty acid; wherein the lipase reaction is performed at a temperature of not more than 25° C.

14 Claims, 4 Drawing Sheets

(56) References Cited

OTHER PUBLICATIONS

U.S. Non Final Office Action corresponding to U.S. Appl. No. 13/700,647 dated Apr. 25, 2014.
"Definition of Room Temperature", The American Heritage Dictionary of the English Language, 2016.
"Medical Definition of Room Temperature", Merrian-Webster Medical Dictionary, 2016.
Holldorsson et al, "Lipase selectivity toward fatty acids commonly found in fish oil" Eur. J. Lipid Sci. Technol., vol. 106, No. 2, 2004, pp. 79-87.
Partial Supplementary European Search Report corresponding to Application No. 11786737.4-1501/2578691 PCT/JP2011/062170, dated May 30, 2016.
Sun et al., "Lipase-Assisted Concentration of n-3 Polyunsaturated Fatty Acids from Viscera of Farmed Atlantic Salmon (*Salmo salar* L.)" Journal of Food Science, vol. 67, No. 1, 2002, pp. 130-136.
Colin F. Moffat et al., "The Production of Fish Oils Enriched in Polyunsaturated Fatty Acid-Containing Triglycerides", Journal of the American Oil Chemists Society, vol. 70, No. 2, Feb. 1993, pp. 133-138.
Extended European Search Report corresponding to Application No. 11786737.4-1501/2578691 PCT/JP2011/062170; dated Oct. 20, 2016.
T. Okada et al., "Production of n-3 Polyunsaturated Fatty Acid Concentrate from Sardine Oil by Immobilized Candida rugosa Lipase" Journal of Food Science vol. 73, Nr. 3, 2008, pp. C146-C150.
F. Thevenieau et al., "Microorganisms as sources of oils," OCL Journals, Jul. 2013, pp. 1-8.
V. Patil et al., "Fatty acid composition of 12 microalgae for possible use in aquaculture feed," Springer Science and Business Media B.V.; May 2006, pp. 1-9.

* cited by examiner

METHOD FOR PRODUCING OIL CONTAINING POLYUNSATURATED FATTY ACID USING LIPASE

CROSS REFERENCE TO RELATED APPLICATIONS

The present application is a continuation application of U.S. patent application Ser. No. 13/700,647, filed on Nov. 28, 2012, the entire contents of which are incorporated herein by reference and priority to which is hereby claimed. Application Ser. No. 13/700,647 is the U.S. National stage of application No. PCT/JP2011/062170, filed on 27 May 2011. Priority under 35 U.S.C. § 119(a) and 35 U.S.C. § 365(b) is claimed from Japanese Application No. 2010-122688, filed 28 May 2010, the disclosure of which are also incorporated herein by reference.

TECHNICAL FIELD

The present invention relates to a method for producing oil containing polyunsaturated fatty acid using lipase reactions.

BACKGROUND ART

In addition to being nutrients that are essential for growth of vertebrates, including humans, polyunsaturated fatty acids in recent years have been frequently reported to be involved in cardiovascular diseases and inflammatory diseases. There have been many reports of findings that the intake of n-3 type polyunsaturated fatty acids, such as docosahexaenoic acid and eicosapentaenoic acid, is particularly useful for human health. There have been reports that the ratio of intake amount of n-3 type polyunsaturated fatty acid to intake amount of n-6 type polyunsaturated fatty acid is important. The industrialized world is characterized by a trend of decreased intake of n-3 type polyunsaturated fatty acids and a trend of increased intake of calories, saturated fatty acids, and n-6 type polyunsaturated fatty acids. This trend is considered to be related to various types of lifestyle-related diseases.

Fish oil is an oil that is rich in n-3 type polyunsaturated fatty acids. The intake of such fish oil is widely recommended, and methods are being devised for the concentration of the n-3 type polyunsaturated fatty acids in fish oil for more efficient intake of n-3 type polyunsaturated fatty acids. The concentration of polyunsaturated fatty acids using lipase reactions is one such method.

Lipases are enzymes that catalyze hydrolysis reactions to decompose oils into free fatty acids and glycerin. Various types of animals and plants and microorganisms are known to have lipases. A given type of lipase does not act similarly for all fatty acids, and the reactivity of a given lipase will vary according to bond position in the glyceride, carbon chain length of the fatty acid, number of double bonds, or the like. It is thus possible to selectively hydrolyze fatty acids using such lipases, and as a result, it becomes possible to concentrate a specific fatty acid within the glyceride fraction. For example, when a lipase produced by a kind of the genus *Candida* is used, it is known that hydrolysis reaction of fish oil results in concentration of polyunsaturated fatty acids, such as docosahexaenoic acid or the like, in the undecomposed glyceride fraction (Patent Document 1).

Hydrolysis reaction by lipase in this manner is a method that is effective for the concentration of polyunsaturated fatty acids. The concentration of polyunsaturated fatty acid in the glyceride fraction increases with progress of hydrolysis with respect to fatty acids other than those of the target polyunsaturated fatty acid. However, as the concentration in the glyceride fraction of the polyunsaturated fatty acid increases, the hydrolysis reaction slows down in practice, and excess enzyme must be added in order that the hydrolysis reaction proceed further. Although the hydrolysis reaction proceeds further when an excess of enzyme has been added, such excess addition then results in a lowering of yield due to hydrolysis reaction of the target polyunsaturated fatty acid and a lowering of the concentration effect as hydrolysis increases. Moreover, lipase gradually loses activity with the passage of hydrolysis reaction time. It is thus possible to further promote hydrolysis by removing the deactivated enzyme and repeating the reaction using fresh enzyme. However, even in this case, there is a marked decline of yield when the degree of hydrolysis is excessive, and the concentration effect for the target polyunsaturated fatty acid is lost.

When *Candida cylindracea*-derived lipase is used for hydrolysis of fish oil, it is possible to increase the acid value of the hydrolyzed oil by increasing the utilized amount of lipase, by prolonging the reaction time, or by repeatedly performing hydrolysis using lipase. However, it is reported that although concentration of the target polyunsaturated fatty acid proceeds, when the acid value exceeds roughly 160, the degree of concentration of polyunsaturated fatty acid conversely decreases (Patent Document 1). That is to say, this means that the frequency of hydrolysis of the target polyunsaturated fatty acid becomes higher when the concentration of the target polyunsaturated fatty acid is promoted by excess hydrolysis reaction, and the proportion of loss of the target polyunsaturated fatty acid increases as concentration factor increases. Thus, at a certain point, the target polyunsaturated fatty acid concentration factor stops increasing, and there is decline in the target polyunsaturated fatty acid concentration. Of course, promotion of hydrolysis may cause a lowering of yield of glycerides. Thus, a limit point occurs in the concentration of a polyunsaturated fatty acid utilizing the hydrolysis by lipase. The added amount of enzyme, reaction time, or the like must be set to obtain a balance between the obtained oil product yield and efficiency of concentration of the target fatty acid.

Optimum temperature of the enzyme reaction is known to depend on the enzyme, and reactions are performed within the temperature range. Although lipase reacts within the temperature range thereof, viscosity of the target oil of the lipase reaction increases at low temperature, and the effectiveness of stirring the oil and enzyme-containing water worsens. Thus, the reaction is normally performed at from 30 to 40° C. For example, when *Candida cylindracea*-derived lipase is used for concentration of polyunsaturated fatty acid, the reaction temperature used in the working examples of Patent Document 1 (filed in 1982) was room temperature, and thereafter reaction temperatures were set in Patent Documents 2 to 7 (filed in 1988, 1993, 1994, 1995, 1996, and 1999, respectively) to 37, 37, 37, 30, 35, and 35° C., respectively.

CITATION LIST

Patent Documents

Patent Document 1: Japanese Examined Patent Application Publication No. H4-16519
Patent Document 2: Japanese Unexamined Patent Application Publication No. H1-269496

Patent Document 3: Japanese Unexamined Patent Application Publication No. H7-51075

Patent Document 4: Japanese Unexamined Patent Application Publication No. H7-268382

Patent Document 5: Japanese Unexamined Patent Application Publication No. H8-214892

Patent Document 6: WO98/18952

Patent Document 7: Japanese Unexamined Patent Application Publication No. 2001-54396

SUMMARY OF INVENTION

Technical Problem

Although various types of methods have been investigated for the production of an oil containing polyunsaturated fatty acids using the lipase reaction in the above described manner, the present invention focuses on the saturated fatty acids of the oil containing the polyunsaturated fatty acids. Oils having a high concentration of polyunsaturated fatty acid are used for intake of useful components such as docosahexaenoic acid (abbreviated hereinafter as "DHA"), eicosapentaenoic acid (abbreviated hereinafter as "EPA"), or the like. When such oils are ingested, it is thought the content of untargeted or undesirable saturated fatty acids is preferably as low as possible. The problem of the present invention is to provide an oil containing polyunsaturated fatty acids that has a further decreased content of saturated fatty acids.

Solution to Problem

During investigations to find out whether there was further margin for improvement of yield, composition, or the like of the lipase reaction, the inventors of the present invention achieved the present invention by discovery of the ability to obtain unexpected results by adjustment of reaction temperature, which is a factor that had heretofore not been considered by anyone and for which thinking had become entrenched (i.e. thinking that from 30 to 40° C. was the optimum temperature).

The gist of the present invention is the method for lowering of the saturated fatty acid content of the below listed (1) and (2), and the glyceride having a low saturated fatty acid content of (3) to (14).

(1) A method for lowering saturated fatty acid content, the method include the step of concentrating polyunsaturated fatty acid using a lipase having low reactivity for the polyunsaturated fatty acid to react with a glyceride containing a polyunsaturated fatty acid; where the lipase reaction is performed at a temperature of not more than 25° C.

(2) The method of (1); where the lipase is derived from a microorganism selected from among a group including microorganisms belonging to the genera Candida, Alcaligenes, Burkholderia, Pseudomonas, Thermomyces, and Rhizomucor.

(3) A glyceride containing a polyunsaturated fatty acid, of which saturated fatty acid fraction is not more than 12 area percent, and which is produced by a method comprising the step of concentrating polyunsaturated fatty acid using a lipase having low reactivity for the polyunsaturated fatty acid to react with a glyceride containing a polyunsaturated fatty acid; wherein the lipase reaction is performed at a temperature of not more than 25° C.

(4) The glyceride containing the polyunsaturated fatty acid of (3); where the lipase is derived from a microorganism selected from among a group including microorganisms belonging to the genera Candida, Alcaligenes, Burkholderia, Pseudomonas, Thermomyces, and Rhizomucor.

(5) A glyceride produced by concentrating a polyunsaturated fatty acid by lipase reaction; where content of docosahexaenoic acid in the glyceride is not less than 46 area percent; and content of saturated fatty acids in the glyceride is not more than 12 area percent.

(6) The glyceride of (5); where content of docosahexaenoic acid in the glyceride is not less than 46 area percent.

(7) The glyceride of (5) or (6); where content of saturated fatty acids is not more than 10 area percent.

(8) The glyceride of any one of (5) to (7); where content of palmitic acid is not more than 8 area percent.

(9) The glyceride of (8); where content of palmitic acid is not more than 6 area percent.

(10) The glyceride of any one of (5) to (9); where the fraction of triglyceride in the glyceride is not less than 80 area percent.

(11) The glyceride of (10); where the fraction of triglyceride in the glyceride is not less than 85 area percent.

(12) A glyceride having polyunsaturated fatty acid concentrated by lipase reaction; where content of eicosapentaenoic acid in the glyceride is not less than 25 area percent; and content of saturated fatty acids is not more than 20 area percent.

(13) The glyceride of (12); where content of eicosapentaenoic acid in the glyceride is not less than 28 area percent.

(14) The glyceride of (12) or (13); where content of the saturated fatty acids is not more than 17 area percent.

The expression "area percent" in the present invention indicates the content fraction of a peak of a component as the ratio relative to the total peak area of all peak areas of the various components in an analytical graph using gas chromatography or thin-layer chromatography/flame ionization detector (TLC/FID) of a mixture of glyceride ingredients composed of various types of fatty acids. The fatty acid composition was determined by gas chromatography by the method indicated in the working examples. The lipid composition was determined using TLC/FID.

Advantageous Effects of Invention

According to the method of the present invention, the polyunsaturated fatty acid such as EPA, DHA, or the like may be concentrated, and a glyceride may be produced that has a low saturated fatty acid content. It is possible to decrease the amount of intake of excess saturated fatty acid during the ingestion of polyunsaturated fatty acid desirable for health.

DESCRIPTION OF EMBODIMENTS

Figure 1:
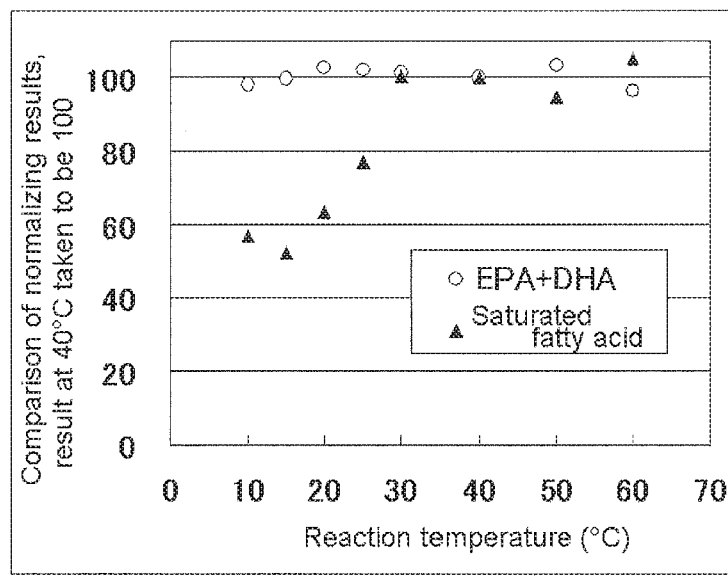
FIG. 1 is a graph showing proportions of saturated fatty acid and EPA+DHA contained in the glyceride fraction treated with lipase at each reaction temperature in Working Example 1, normalized such that results for the reaction at 40° C. are 100.

The following is a detailed explanation of the invention. The polyunsaturated fatty acid of the present invention is taken to mean a fatty acid having at least 18 carbon atoms and having at least 3 double bonds, and more preferably a fatty acid having at least 20 carbon atoms and having at least 3 double bonds. Such fatty acids are exemplified by α-linolenic acid (18:3, n-3), γ-linolenic acid (18:3, n-6), arachidonic acid (20:4, n-6), dihomo-γ-linolenic acid (20:3, n-6), eicosapentaenoic acid (20:5, n-3), docosapentaenoic acid (22:5, n-6), docosahexaenoic acid (22:6, n-3), or the like. These polyunsaturated fatty acids are known to be contained in large amounts in certain microorganism oils, plant oils, marine animal oils, or the like. Such polyunsaturated fatty acids are exemplified by: marine animal oils such as those of fishes including sardine, tuna, bonito, and the like and crustaceans including krill and the like; plant oils such as *perilla* oil, flaxseed oil, soybean oil, rapeseed oil; and oils produced by microorganisms belonging to the genera *Mortierella, Penicillium, Aspergillus, Rhodotorula, Fusarium*; or the like.

The term "saturated fatty acid" for the present invention is a saturated fatty acid having 14, 16, or 18 carbon atoms. Although such saturated fatty acids are important nutrients as sources of calories, the intake of these saturated fatty acids from normal foods of the modern diet is often in excess of the required amount, and these saturated fatty acids are considered to be fatty acids that should not be ingested in excess.

The glycerides containing polyunsaturated fatty acids of the present invention are triglycerides, diglycerides, and monoglycerides containing as constituent fatty acids the aforementioned polyunsaturated fatty acids. The aforementioned microorganism oils, plant oils, and marine animal oils are triglycerides that include polyunsaturated fatty acids.

Any lipase may be used for the present invention as long as the lipase has low activity with respect to polyunsaturated fatty acid and has the property of concentrating polyunsaturated fatty acid in the undecomposed glyceride fraction by the hydrolysis reaction. For example, lipases derived from *Candida cylindracea* and *Candida rugosa* concentrate DHA, arachidonic acid, and γ-linolenic acid. Lipase derived from *Rhizomucor miehei* has the ability to concentrate DHA. Lipases derived from *Alcaligenes* sp. and *Pseudomonas* sp. have the ability to concentrate EPA. All of these lipases are commercially marketed and may be readily obtained. As may be required, these lipases may be fixed prior to use. For example, the utilized lipase may be derived from *Candida cylindracea*, i.e. a lipase derived from the genus *Candida*. Lipase derived from *Candida cylindracea* is exemplified by Lipase OF, produced by Meito Sangyo Co., Ltd. Alternative lipases are exemplified by lipases obtained from microorganisms belonging to *Alcaligenes* sp. (Lipase QLM, Lipase QLC, Lipase PL, all produced by Meito Sangyo Co., Ltd.), lipases obtained from microorganisms belonging to *Burkholderia cepacia* (Lipase PS, produced by Amano Enzyme Inc.), lipases obtained from microorganisms belonging to *Pseudomonas fluorescens* (Lipase AK, produced by Amano Enzyme Inc.), lipases obtained from microorganisms belonging to *Thermomyces lanuginosa* (Lipozyme TLIM, produced by Novozymes), or the like.

The utilized amount of lipase relative to 1 g of triglyceride is normally from 10 to 2,000 units, and preferably is from 200 to 700 units. Here, 1 unit is the amount of enzyme that releases 1 μmol of fatty acid in 1 minute. The hydrolysis reaction using lipase requires that the reaction be performed in the presence of a sufficient amount of water for expression of the hydrolysis activity of lipase. Relative to the triglyceride, the amount of water present is from 10 to 200 percent by weight, and preferably is from 50 to 150 percent by weight.

In order to suppress deterioration of the fatty acids, deactivation of the enzyme, or the like, the hydrolysis is preferably performed under an inert gas atmosphere, such as dry nitrogen or the like. An antioxidant may preferably also be used, such as tocopherol, ascorbic acid, t-butyl hydroquinone, or the like.

The hydrolysis reaction is performed at a temperature of not more than 25° C., preferably from 10 to 25° C., and more preferably from 15 to 20° C. Although as low a temperature as possible is preferred for causing a lowering of the content of saturated fatty acids, at temperatures of not more than 10° C., the viscosity of the oil increases and the rate of the enzyme reaction itself declines excessively. Thus a temperature of roughly from 15 to 20° C. is most preferable. In the case of a large-scale reaction, the reaction phase temperature is preferably set to be from 15 to 20° C., and the reaction may be performed while maintaining temperature within a range of about ±5° C. The hydrolysis reaction is performed in a flow or the like caused by stirring, injecting an inert gas or the like.

Hydrolysis is performed until the proportion of docosahexaenoic acid contained in the constituent fatty acids reaches the target value. Reaction conditions differ according to the raw material oil. For example, in the case of use of tuna oil (containing about 23 percent DHA) as the raw material, the reaction time is preferably at least 7 hours, and normally hydrolysis is performed for 5 to 24 hours. The proportion of docosahexaenoic acid then becomes not less than 46 area percent by a single lipase reaction. The reaction may also be performed for a longer time. There were no adverse effects even when the reaction was performed for 65 hours as indicated in the working examples. Moreover, acid value may be used as an indicator showing the degree of hydrolysis. The fraction of docosahexaenoic acid normally becomes at least 46 area percent when the acid value becomes not less than 140.

By performing hydrolysis in this manner, a mixture of hydrolysate and unreacted triglyceride is obtained as the reaction liquid. As hydrolysis by lipase that has low reactivity toward polyunsaturated fatty acid progresses, the proportion of polyunsaturated fatty acids (i.e. docosahexaenoic acid, eicosapentaenoic acid, or the like) in the constituent fatty acids of the unreacted triglycerides and partial glycerides within the reaction liquid becomes high. The concentration continues until the docosahexaenoic acid concentration at the time of completion of hydrolysis becomes at least 40 area percent. On the other hand, most of the free fatty acids are fatty acids other than the polyunsaturated fatty acids.

After completion of the hydrolysis, the oil layer of the reaction liquid is obtained by removing the aqueous layer containing lipase, glycerin, and the like via centrifugal separation or the like. Then, the free fatty acids are removed. Methods that may be adopted for the separation and removal of the free fatty acids include known methods such as the method of removal as alkaline salts, method using a liquid chromatographic device, fractional distillation method, and crystal separation method. However, molecular distillation and steam distillation are preferred.

By removal of the free fatty acid, a glyceride mixture is obtained of partial glycerides and triglycerides containing docosahexaenoic acid at high concentration.

By the low temperature reaction of the present invention, it is possible to obtain a glyceride where docosahexaenoic acid is concentrated to a concentration of at least 40 area percent, and further concentrated to at least 46 area percent. Moreover, a glyceride may be obtained where the total amounts of saturated fatty acids having 14, 16, and 18 carbon atoms is not more than 12 area percent, and preferably is not more than 10 area percent. Particularly, the concentration of palmitic acid (having 16 carbon atoms), which is contained at the highest concentration among saturated fatty acids, is not more than 8 area percent, and preferably is not more than 6 area percent. When the lipase reaction was performed at low temperature, the proportion of triglyceride in the lipid composition of the glyceride in the obtained reaction oil became high. When a raw material oil were used that contained a large amount of docosahexaenoic acid such as the tuna refined fish oil and bonito refined fish oil indicated in the working examples, the proportion of triglyceride at 40° C. was about the 70 area percent level. In a low temperature reaction, the obtained proportion of triglyceride was not less than 80 area percent.

By performing deacidification, decoloration, and deodorizing treatment of the lipase reaction oil of the present invention, polyunsaturated fatty acids are concentrated, and a glyceride may be obtained that has a reduced content of saturated fatty acids. The processing methods of deacidification, decoloration, and deodorizing may be any methods. Deacidification treatment is performed by distillation. Decolorization treatment is performed by treatment using activated earth, activated carbon, or the like. Deodorization treatment is performed by steam distillation or the like.

Monoglycerides are simultaneously removed during deacidification treatment by distillation, and it is thus possible to further increase the proportion of triglycerides in the obtained oil. It is possible to obtain a proportion of triglyceride of not less than 85 area percent, and preferably not less than 90 area percent.

The present invention will now be explained in greater detail through the use of working examples, but is in no way limited to these working examples.

EXAMPLES

Measurements of fatty acid composition and acid value were performed by the below described methods for each of the working examples.

Measurement of Fatty Acid Composition

Fatty acid composition of the fish oil used as the raw material was measured by ethyl esterification of the fish oil and measurement by gas chromatography. That is to say, 1 mL of 1 N sodium ethylate in ethanol solution was added to 40 µL of fish oil, and the mixture was agitated for about 30 seconds. Thereafter, 1 mL of 1N hydrochloric acid was added to neutralize the mixture, and 2 mL of hexane and 3 mL of saturated ammonium sulfate aqueous solution were added. After stirring and then allowing the mixture to sit, content of the supernatant was measured by gas chromatography.

The fatty acid composition of the glyceride fraction of the oil after the enzyme reaction was measured by ethyl esterification of the glyceride fraction, removal of free fatty acids (i.e. byproduct of the enzyme reaction), and measurement by gas chromatography. That is to say, 1 mL of 1N sodium ethylate in ethanol solution was added to 70 µL of reaction oil, and the mixture was agitated for about 30 seconds. Thereafter, 1 mL of 1N hydrochloric acid was added to neutralize the mixture, and 700 µL of hexane and 3 mL of saturated ammonium sulfate aqueous solution were added. After stirring and then allowing the mixture to sit, the supernatant containing ethyl esters and free fatty acids was collected. Free fatty acids were removed from the obtained supernatant by the below described procedure. To 700 µL of hexane solution containing the recovered supernatant, i.e. ethyl esters and free fatty acids, was added 10 to 20 µL of triethyl amine, and the mixture was mixed by shaking. Thereafter, the entire amount of the mixture was loaded into a solid phase extraction cartridge (Varian Inc., Bond Elut SI, 100 mg, 1 mL), and the ethyl esters were eluted to remove the free fatty acids using 1 mL of mixed solution of hexane and ethyl acetate (hexane:ethylacetate=50:1 volume ratio). This eluate was measured by gas chromatography.

Gas Chromatography Analysis Conditions

Equipment type: Agilent 6850 GC system (Agilent Technologies, Inc.)

Column: DB-wax J & W 122-7032

Column temperature: 200° C.

Injection temperature: 300° C.

Injection method: split

Split ratio: 50:1

Detector temperature: 300° C.

Detector: FID

Carrier gas: helium (2.9 mL/min, constant flow)

Measurement of Acid Value (AV)

For the working examples of the present invention, acid value (AV) was measured based on Standard Methods for the Analysis of Fats, Oils, and Related Materials (2003 edition, edited by the Japan Oil Chemists' Society).

About 0.5 g of oil was dissolved in ethanol, a drop of phenolphthalein was added, and titration-neutralization was performed using a 1N sodium hydroxide aqueous solution. The acid value was calculated based on the following formula.

$$AV = \text{titration amount (mL)} \times 56.11 / \text{sample mass (g)}$$

Measurement of Lipid Composition

Measurement of lipid composition was performed by thin-layer chromatography/flame ionization detector (TLC/FID, Iatroscan, Mitsubishi Kagaku Iatron, Inc.). 20 µL of oil was dissolved in 1 mL of hexane, and 0.5 µL of this solution was loaded into a Chromarod. A mixed solution of hexane, diethyl ether, and acetic acid (hexane:diethyl ether:acetic acid=70:30:0.1 volume ratio) was used as the development solvent (35 min development time). Analysis was performed using the Iatroscan.

Working Example 1

To 3 mL of refined fish oil 1 (deacidified tuna oil, Nippon Suisan Kaisha, Ltd.) were added 1.5 mL of water and 5 mg of Lipase OF (Meito Sangyo Co., Ltd., 600 units/mL oil). A magnetic stirrer was used to stir the mixture for 14 hours in a incubator at from 10 to 60° C. After the 14 hours of stirring, about 2 mL of the reaction oil was sampled, and the lipase was deactivated by heating for 10 minutes at 80° C. Thereafter, the mixture was separated into an oil layer and aqueous layer using a centrifugal separator (40° C., 1,800 g, 10 min) to obtain the reaction oil.

The fatty acid composition (area percent) of the glyceride fraction of the obtained reaction oil, the acid value, and the fatty acid composition of the refined fish oil 1 (area percent) are shown in Table 1. The total of the myristic acid (C14:0), palmitic acid (C16:0), and stearic acid (C18:0) content (area percent) in the glyceride fraction obtained during gas chromatography is indicated as the saturated fatty acid content (hereinafter, "saturated fatty acid content" described in the working examples is taken to mean this value).

At reaction temperatures of from 30 to 60° C., content of the saturated fatty acids was about 15 percent. In contrast, content of the saturated fatty acids was 11.40 percent at 25° C., was 9.36 percent at 20° C., was 7.74 percent at 15° C., and was 8.42 percent at 10° C. The content of saturated fatty acid decreased greatly when the reaction was performed at low temperature. Saturated fatty acid content decreased greatly at from 10 to 25° C. Moreover, reaction rate deteriorated at 10° C. relative to the other temperature conditions, resulting in a low acid value (AV) of 113.9. However, under such conditions, the saturated fatty acid content was low (i.e. 8.42 percent), and acid value was greatly reduced relative to that under 40° C. conditions (acid value (AV) was 125.1) where the hydrolysis reaction proceeded further.

In order to compare the results of decrease of saturated fatty acids with those of the temperature range (near 40° C.) where the lipase hydrolysis reaction is generally carried out, the proportion of such fatty acid content at respective temperatures is shown in FIG. 1, where the total amount of DHA and EPA and the saturated fatty acid content at 40° C. are normalized to 100. From this figure, under 10 to 25° C. temperature conditions, it is understood that there was a great decrease in the saturated fatty acid content, while the EPA and DHA contents remained high.

Working Example 2

100 g of water and 320 mg of Lipase OF (Meito Sangyo Co., Ltd., 640 units/mL oil) were added to 200 g of refined fish oil 2 (deacidified tuna oil, Nippon Suisan Kaisha, Ltd.), and the mixture was stirred for 20 hours at from 10 to 40° C. using a stirrer blade. After 20 hours of stirring, the reaction oil was heated to 80° C. for 15 min to deactivate lipase, and a supernatant reaction oil was obtained.

The fatty acid composition (area percent) of the glyceride fraction of the obtained reaction oil, the acid value, and the fatty acid composition (area percent) of the refined fish oil 2 are shown in Table 2 (only typical fatty acids are shown in the fatty acid composition). The glyceride content here was calculated by calculating the free fatty acid content equivalent to oleic acid from the acid value, and then subtracting the free fatty acid content from the total reaction oil. Moreover, the total of the myristic acid (C14:0), palmitic acid (C16:0), and stearic acid (C18:0) content (area percent) in the glyceride fraction obtained during gas chromatography is indicated as the saturated fatty acid content.

In comparison to 35 and 40° C., there was a great decrease in the saturated fatty acid content at from 10 to 25° C.

TABLE 1

| Reaction temperature (° C.) | | 10 | 15 | 20 | 25 | 30 | 40 | 50 | 60 | Refined fish oil 1 |
|---|---|---|---|---|---|---|---|---|---|---|
| Fatty acid | C14:0 | 1.55 | 1.59 | 1.64 | 1.68 | 1.71 | 1.74 | 1.64 | 1.81 | 2.65 |
| composition | C14:1 | 0.27 | 0.27 | 0.25 | 0.25 | 0.16 | 0.15 | 0.14 | 0.21 | 0.26 |
| (area percent) | C16:0 | 4.88 | 4.53 | 5.94 | 7.40 | 10.29 | 10.20 | 9.67 | 9.80 | 17.38 |
| | C16:1 | 3.13 | 3.17 | 2.99 | 2.89 | 2.91 | 3.01 | 2.84 | 2.62 | 4.70 |
| | C16:2 | 1.44 | 1.38 | 1.31 | 1.17 | 1.08 | 1.13 | 0.98 | 1.35 | 1.22 |
| | C18:0 | 1.99 | 1.62 | 1.78 | 2.31 | 2.85 | 2.88 | 2.71 | 3.95 | 4.96 |
| | C18:1 n-9 | 11.33 | 11.26 | 10.60 | 10.05 | 9.42 | 9.69 | 9.37 | 8.59 | 16.34 |
| | C18:1 n-7 | 1.74 | 1.80 | 1.68 | 1.56 | 1.43 | 1.47 | 1.42 | 1.51 | 2.41 |
| | C18:2 n-6 | 0.82 | 0.83 | 0.71 | 0.67 | 0.65 | 0.67 | 0.67 | 0.59 | 1.16 |
| | C18:3 n-3 | 0.28 | 0.00 | 0.26 | 0.26 | 0.25 | 0.26 | 0.25 | 0.37 | 0.31 |
| | C18:3 n-6 | 0.40 | 0.41 | 0.35 | 0.36 | 0.36 | 0.37 | 0.34 | 0.33 | 0.53 |
| | C18:4 n-3 | 1.37 | 1.36 | 1.33 | 1.21 | 1.12 | 1.20 | 1.00 | 1.35 | 0.82 |
| | C20:0 | 0.27 | 0.25 | 0.26 | 0.27 | 0.29 | 0.29 | 0.33 | 0.36 | 0.29 |
| | C20:1 | 1.81 | 1.75 | 0.53 | 0.50 | 2.03 | 2.09 | 2.29 | 3.02 | 2.64 |
| | C20:3 n-3 | 0.21 | 0.21 | 0.20 | 0.18 | 0.48 | 0.43 | 0.00 | 0.26 | 0.24 |
| | C20:4 n-6 | 2.78 | 2.80 | 2.83 | 2.72 | 2.70 | 2.74 | 2.70 | 2.78 | 1.82 |
| | C20:4 n-3 | 0.61 | 0.59 | 0.52 | 0.47 | 0.41 | 0.43 | 0.43 | 0.70 | 0.53 |
| | EPA | 7.61 | 7.32 | 6.98 | 6.24 | 5.79 | 5.93 | 6.06 | 9.38 | 6.55 |
| | C22:5 n-3 | 2.33 | 2.34 | 2.55 | 2.48 | 2.63 | 2.61 | 2.44 | 2.29 | 1.60 |
| | DHA | 44.32 | 45.52 | 47.47 | 47.84 | 47.86 | 47.06 | 48.76 | 41.56 | 23.61 |
| EPA + DHA (area percent) | | 51.93 | 52.84 | 54.45 | 54.08 | 53.65 | 52.98 | 54.82 | 50.95 | 30.17 |
| Saturated fatty acid (area percent) (C14:0 + C16:0 + C18:0) | | 8.42 | 7.74 | 9.36 | 11.40 | 14.85 | 14.81 | 14.02 | 15.56 | 24.99 |
| Acid value (AV) | | 113.9 | 129.7 | 124.5 | 125.2 | 124.2 | 125.1 | 112.4 | 91.6 | |

TABLE 2

| Reaction temperature (° C.) | | 10 | 15 | 20 | 25 | 30 | 35 | 40 | Refined fish oil 2 |
|---|---|---|---|---|---|---|---|---|---|
| Fatty acid composition (area %) | C14:0 | 1.88 | 1.68 | 1.78 | 1.75 | 1.73 | 1.57 | 1.56 | 2.56 |
| | C16:0 | 7.15 | 4.57 | 5.13 | 6.73 | 8.54 | 11.84 | 11.88 | 20.52 |
| | C16:1 | 3.99 | 3.73 | 3.69 | 3.35 | 3.27 | 2.83 | 2.81 | 4.77 |
| | C18:0 | 3.07 | 2.19 | 2.22 | 2.82 | 3.36 | 3.49 | 3.49 | 5.76 |
| | C18:1 | 15.20 | 13.94 | 13.65 | 12.43 | 11.78 | 9.82 | 9.85 | 17.16 |
| | C18:2 n-6 | 0.95 | 0.89 | 0.87 | 0.76 | 0.73 | 0.64 | 0.61 | 1.09 |
| | C18:4 n-3 | 0.91 | 0.96 | 0.92 | 0.84 | 0.83 | 0.75 | 0.76 | 0.60 |
| | C20:4 | 3.04 | 3.16 | 3.10 | 3.00 | 2.95 | 2.82 | 2.77 | 2.19 |
| | EPA | 5.75 | 5.68 | 5.44 | 5.14 | 4.77 | 4.31 | 4.27 | 5.11 |
| | C22:5 n-3 | 1.94 | 2.07 | 2.08 | 2.03 | 2.02 | 1.97 | 1.97 | 1.35 |
| | DHA | 41.38 | 46.34 | 46.52 | 46.63 | 45.78 | 46.23 | 46.12 | 24.22 |
| EPA + DHA (area percent) | | 47.13 | 52.02 | 51.96 | 51.77 | 50.55 | 50.54 | 50.39 | 29.33 |
| Saturated fatty acid (area percent) (C14:0 + C16:0 + C18:0) | | 12.10 | 8.44 | 9.13 | 11.30 | 13.63 | 16.90 | 16.93 | 28.84 |
| Acid value (AV) | | 100.9 | 111.8 | 117.1 | 116.2 | 115.2 | 111.8 | 115.1 | |

Figure 2:
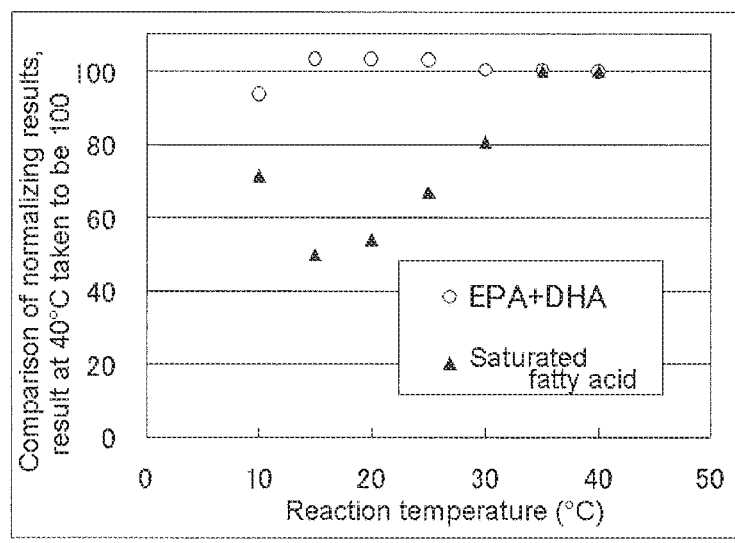
FIG. 2 is a graph showing proportions of saturated fatty acid and EPA+DHA contained in the glyceride fraction treated with lipase at each reaction temperature in Working Example 2, normalized such that results for the reaction at 40° C. are 100.

Similarly to FIG. 1, the aforementioned results are shown in FIG. 2, which shows the EPA and DHA content and the saturated fatty acid content of the glyceride fraction under each temperature condition, when the result for the 40° C. reaction oil is normalized to 100. From this figure, it is understood that, under 10 to 25° C. conditions, there was a great decrease in the saturated fatty acid content, while the EPA and DHA contents remained high.

Working Example 3

4 mL of water and 13.3 mg (600 units/mL oil) or 6.7 mg (300 units/mL oil) of Lipase OF were added to 8 mL of refined fish oil 1, and the mixture was stirred using a stirrer blade. The reaction temperature was set to 20° C. After 2, 5, 8, 14, and 20 hours, a sample was obtained (about 1 to 2 g), and lipase of the sample was deactivated by heating for 10 minutes at 80° C. Thereafter, the mixture was separated into an oil layer and aqueous layer using a centrifugal separator (40° C., 1,800 g, 10 min) to obtain the reaction oil.

Figure 3:
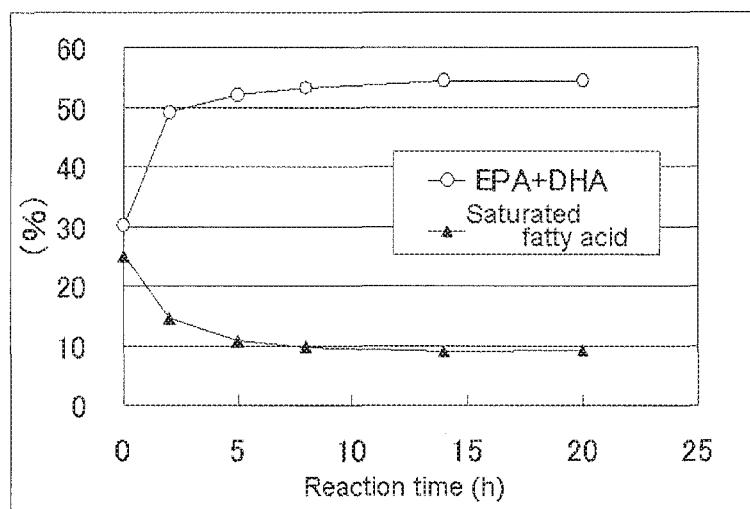
FIG. 3 is a graph showing change over time of saturated fatty acid, EPA, and DHA amounts during the lipase reaction of Working Example 3 (20° C., 600 units/mL oil).
Figure 4:
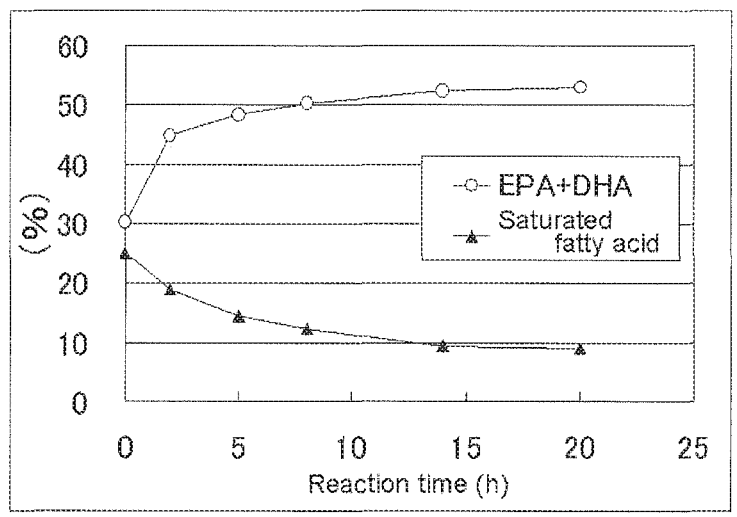
FIG. 4 is a graph showing change over time of saturated fatty acid, EPA, and DHA amounts during the lipase reaction of Working Example 3 (20° C., 300 units/mL oil).

The saturated fatty acid content (area percent) and the EPA and DHA content (area percent) at each time interval are shown in FIGS. 3 and 4. The saturated fatty acid content decreased greatly with reaction time, and the EPA and DHA content increased with reaction time.

Comparative Example 1

Except for setting the reaction temperature to 40° C., the reaction was performed by the same procedure and under the same conditions as Working Example 3 using 600 units/mL of the lipase.

Figure 5:
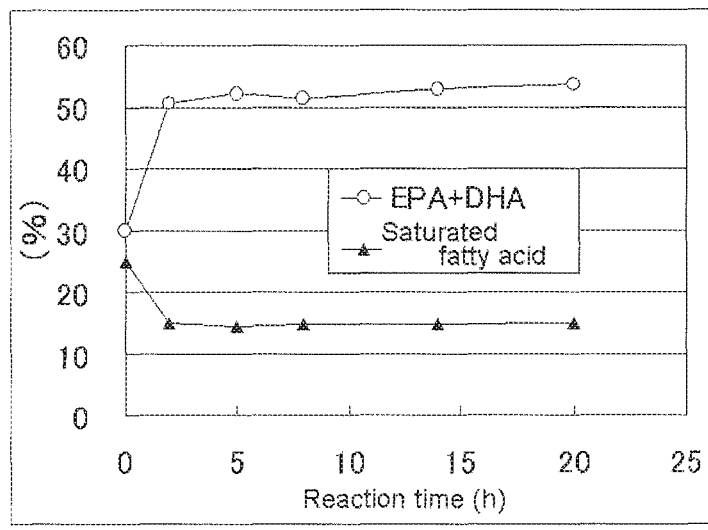
FIG. 5 is a graph showing change over time of saturated fatty acid, EPA, and DHA amounts during the lipase reaction of Comparative Example 1 (40° C., 600 units/mL oil).

Saturated fatty acid content (area percent) and EPA and DHA content (area percent) at each time interval are shown in FIG. 5. Although the saturated fatty acid content decreased down to 15.0 percent at 2 hours of reaction time, further decrease was not found even when the reaction time was further prolonged, and there was a shift to a high saturated fatty acid content of about 15 percent.

Working Example 4 and Comparative Example 2

To 3 mL of refined fish oil 3 (deacidified tuna oil, Nippon Suisan Kaisha, Ltd.) were added 1.5 mL of water and 5 mg of Lipase OF (600 units/mL oil). A magnetic stirrer was used to stir the mixture for 14 hours in a incubator at 20° C. After the 14 hours of stirring, about 2 mL of the reaction oil was sampled, and the lipase was deactivated by heating for 10 minutes at 80° C. Thereafter, the mixture was separated into an oil layer and aqueous layer using a centrifugal separator (40° C., 1,800 g, 10 min) to obtain the reaction oil.

As a comparative example, the reaction was performed under the same conditions as those mentioned above for Working Example 4, except for change of temperature to 40° C. Except for temperature, all conditions and procedures were the same.

Figure 6:
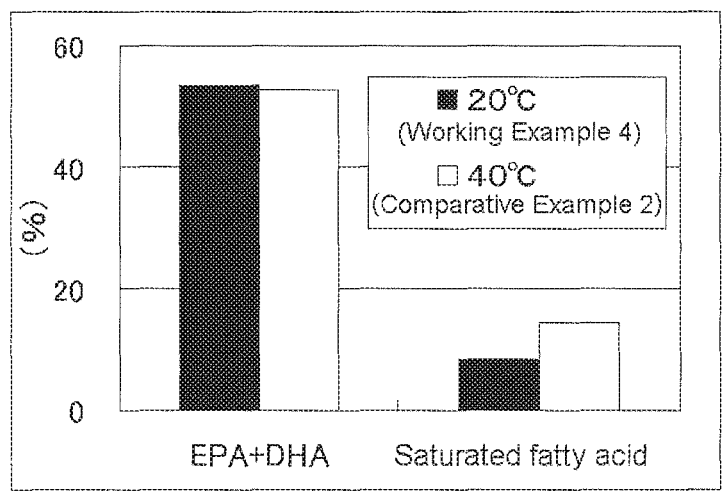
FIG. 6 is a graph showing a comparison of saturated fatty acid, EPA, and DHA amounts in the lipase reaction of Working Example 4 (20° C.) and Comparative Example 2 (40° C.).

The saturated fatty acid content (area percent) and the EPA and DHA content (area percent) of Working Example 4 and Comparative Example 2 are shown in FIG. 6. From this figure, it is understood that the saturated fatty acid content greatly decreased and the EPA and DHA content somewhat increased under the 20° C. temperature condition in comparison to 40° C. temperature condition.

Working Example 5

6,000 L of refined fish oil 4 (deacidified tuna oil, Nippon Suisan Kaisha, Ltd.), 3,000 L of water, and 5 kg of Lipase OF (300 unit/mL oil) were loaded into a reaction vessel, and reaction was carried out by stirring for 21 hours while maintaining temperature at from 20 to 25° C. After the 21 hours of stirring, about 50 g of the reaction oil was sampled, the lipase was deactivated by heating for 10 min at 80° C., and a supernatant reaction oil was obtained.

Figure 7:
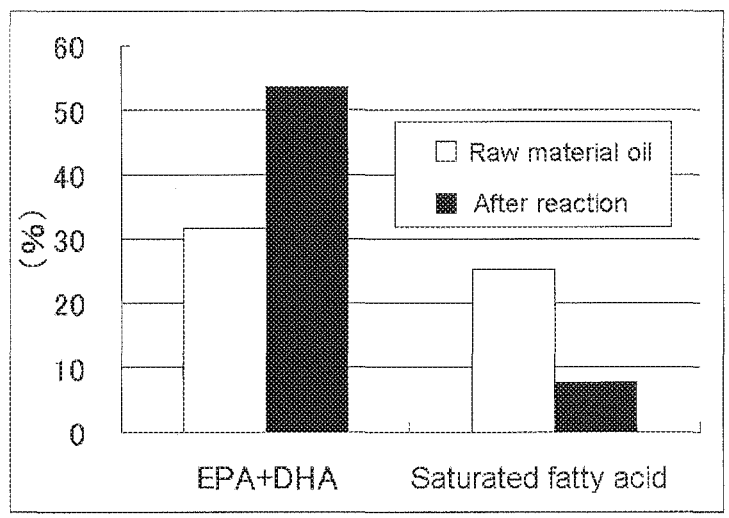
FIG. 7 is a graph showing results of the large-scale reaction of Working Example 5.

Saturated fatty acid content (area percent) and EPA and DHA content (area percent) of the refined fish oil, and saturated fatty acid content (area percent) and EPA and DHA content (area percent) of the glyceride fraction of the reaction oil are shown in FIG. 7. Even when the reaction was performed at a large scale, it was confirmed that EPA and DHA concentration increased and that the saturated fatty acid content decreased greatly to not more than 10 percent.

Working Example 6

Lipid composition (area percent) was measured in the glyceride fraction of the reaction oils produced under the 10, 20, 40, and 50° C. reaction conditions of Working Example 1. As shown in Table 3, it was possible to obtain a triglyceride fraction having a triglyceride proportion of at least 80 area percent when the reaction was performed at 10 and 20° C. On the other hand, the triglyceride proportion was about 72.8 area percent and 59.9 area percent when the reaction was performed at 40 and 50° C., respectively. By performing the lipase reaction at low temperature, in addition to being able to lower the saturated fatty acid content, it was shown possible to increase the triglyceride proportion.

TABLE 3

| Reaction temperature (° C.) | | 10 | 20 | 40 | 50 |
|---|---|---|---|---|---|
| Lipid Composition (%) | Triglyceride | 82.6 | 82.4 | 72.8 | 59.9 |
| | Diglyceride | 15.5 | 14.6 | 18.7 | 30.4 |
| | Monoglyceride | 1.9 | 3.0 | 8.4 | 9.8 |

Working Example 7 and Comparative Example 3

To 2 g of refined fish oil 5 (refined sardine oil, Nippon Suisan Kaisha, Ltd.) were added 2 mL of water and 100 to 600 units/g oil lipase QLM (Meito Sangyo Co., Ltd.). A magnetic stirrer was used to stir the mixture for 17 to 65 hours under 20° C. or 40° C. temperature conditions. Thereafter, the reaction liquid was heated for 15 minutes at 90° C. to deactivate the lipase, and the reaction liquid was separated into an oil layer and aqueous layer using a centrifugal separator (room temperature, 3,000 rpm, 5 min) to obtain the reaction oil.

Acid value of the obtained reaction oil, fatty acid composition (area percent) of the glyceride fraction, degree of hydrolysis (percent), and fatty acid composition (area percent) of the refined fish oil 5 are shown in Table 4. The degree of hydrolysis was calculated by the following formula from the saponification value (206.04) of refined fish oil 5 and the acid value.

Degree of hydrolysis=(acid value/saponification value)×100

Figure 8:
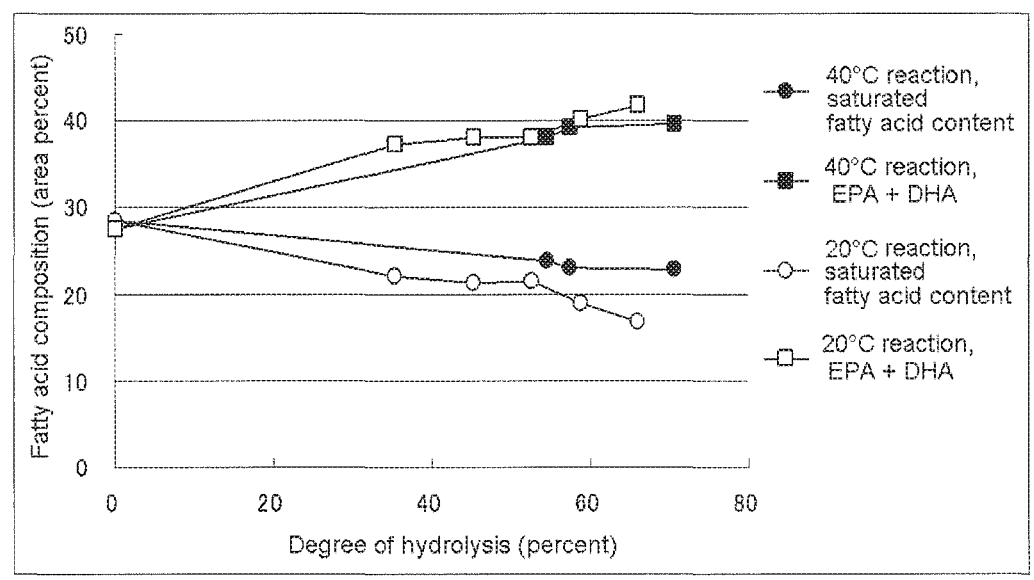
FIG. 8 is a graph showing change over time of saturated fatty acid, EPA, and DHA amounts in the lipase reaction of Working Example 7.

Moreover, the relationship between degree of hydrolysis and fatty acid composition (area percent) is shown in FIG. 8.

Based on Table 4 and FIG. 8, even when the EPA concentration reaction was carried out using Lipase QLM, saturated fatty acid content decreased when the reaction was performed at 20° C. in comparison to 40° C. (i.e. the temperature region where the reaction has been generally performed).

TABLE 4

| | | Reaction temperature | | | | | | | | |
|---|---|---|---|---|---|---|---|---|---|---|
| | | 40° C. | | | 20° C. | | | | | |
| | | Lipase QLM (u/g oil) | | | | | | | | |
| | | 200 | 300 | 600 | 200 | 300 | 600 | 300 | 300 | |
| | | Reaction time | | | | | | | | Refined |
| | | 17 hours | | | 17 hours | | | 41 hours | 65 hours | fish oil 5 |
| Fatty acid composition (area percent) | C14:0 | 6.92 | 6.62 | 6.25 | 7.51 | 7.36 | 7.16 | 7.19 | 7.05 | 7.07 |
| | C16:0 | 14.17 | 13.67 | 13.81 | 12.17 | 11.62 | 11.90 | 9.45 | 7.76 | 17.88 |
| | C18:0 | 2.78 | 2.74 | 2.85 | 2.43 | 2.36 | 2.38 | 2.39 | 2.07 | 3.64 |
| | EPA | 26.64 | 28.01 | 28.92 | 24.28 | 25.17 | 25.58 | 27.75 | 29.74 | 16.86 |
| | DHA | 11.53 | 11.23 | 10.77 | 13.02 | 12.84 | 12.60 | 12.52 | 12.14 | 10.61 |
| EPA + DHA (area percent) | | 38.17 | 39.24 | 39.69 | 37.30 | 38.01 | 38.18 | 40.27 | 41.88 | 27.47 |
| Saturated fatty acid (area percent) (C14:0 + C16:0 + C18:0) | | 23.87 | 23.03 | 22.91 | 22.11 | 21.34 | 21.44 | 19.03 | 16.88 | 28.59 |
| Degree of hydrolysis ((acid value/saponification value) × 100) | | 54.7 | 57.6 | 70.8 | 35.5 | 45.3 | 52.7 | 58.9 | 66.1 | |
| Acid value (AV) | | 112.7 | 118.7 | 145.8 | 73.1 | 93.3 | 108.7 | 121.4 | 136.1 | |

INDUSTRIAL APPLICABILITY

One object of intake of fatty acids having physiological activity (i.e. EPA, DHA, or the like) is to prevent diseases of the heart and vascular system such as hypercholesterolemia or the like. Although saturated fatty acids are important as a source of calories, the modern diet often results in excessive intake of saturated fatty acids, particularly during middle age, and aggressive intake of saturated fatty acids is undesirable. Particularly, for people who need to take preventive measures for heart and vascular system diseases, when highly unsaturated acid is ingested, the amount of co-ingested saturated fatty acid is preferably as low as possible. The oil produced by the present invention concentrates polyunsaturated fatty acid and further reduces the amount of saturated fatty acid. The present invention is thus suitable for use as a health food or supplement for supplying n-3 type polyunsaturated fatty acids.

The invention claimed is:

1. A method for lowering saturated fatty acid content in a glyceride containing a polyunsaturated fatty acid, the method comprising:
   concentrating the polyunsaturated fatty acid using a lipase having low reactivity for the polyunsaturated fatty acid to hydrolyze the glyceride containing the polyunsaturated fatty acid, wherein the glyceride containing the polyunsaturated fatty acid is a marine animal oil glyceride or a microorganism oil glyceride;
   wherein the polyunsaturated fatty acid is a fatty acid having at least 20 carbon atoms and having at least 3 double bonds,
   wherein the hydrolysis by the lipase is performed in the presence of 10 to 200 weight percent of water based on a total weight of the glyceride containing the polyunsaturated fatty acid, and at a temperature from 10° C. to 20° C.,
   wherein the lipase is derived from a microorganism selected from the group consisting of *Candida cylindracea* and *Alcaligenes* sp.; and
   wherein the saturated fatty acid content in the resulting glyceride is less than the saturated fatty acid content in the glyceride prior to the concentrating.

2. A method for preparing a marine animal oil glyceride containing a concentrated polyunsaturated fatty acid, the method comprising:
   concentrating the polyunsaturated fatty acid using a lipase having low reactivity for the polyunsaturated fatty acid to hydrolyze the marine animal oil glyceride containing the polyunsaturated fatty acid;
   wherein content of saturated fatty acid in the resulting marine animal oil glyceride is not more than 12 area percent;

wherein the hydrolysis by the lipase is performed in the presence of 10 to 200 weight percent of water based on a total weight of the marine animal oil glyceride containing the polyunsaturated fatty acid, and at a temperature from 10° C. to 20° C.; and wherein the lipase is derived from *Candida cylindracea*.

3. The method according to claim 2, wherein content of docosahexaenoic acid in the resulting glyceride is not less than 40 area percent.

4. The method according to claim 2, wherein content of docosahexaenoic acid in the resulting glyceride is not less than 46 area percent.

5. The method according to claim 2, wherein content of saturated fatty acids in the resulting glyceride is not more than 10 area percent.

6. The method according to claim 2, wherein content of palmitic acid in the resulting glyceride is not more than 8 area percent.

7. The method according to claim 2, wherein content of palmitic acid in the resulting glyceride is not more than 6 area percent.

8. The method according to claim 2, wherein content of triglyceride in the resulting glyceride is not less than 80 area percent.

9. The method according to claim 2, wherein content of triglyceride in the resulting glyceride is not less than 85 area percent.

10. The method according to claim 1, wherein the marine animal oil glyceride is derived from a fish, a crustacean, or a combination thereof.

11. The method according to claim 2, wherein the marine animal oil glyceride is derived from a fish, a crustacean, or a combination thereof.

12. The method according to claim 1, wherein the glyceride containing the polyunsaturated fatty acid is the microorganism oil glyceride produced by microorganisms belonging to the genera *Mortierella, Penicillium, Aspergillus, Rhodotorula*, or *Fusarium*.

13. The method according to claim 1, wherein the glyceride containing the polyunsaturated fatty acid is the microorganism oil glyceride produced by *Mortierella* sp.

14. A method for preparing a microorganism oil glyceride containing a concentrated polyunsaturated fatty acid, the method comprising:

concentrating the polyunsaturated fatty acid using a lipase having low reactivity for the polyunsaturated fatty acid to hydrolyze the microorganism oil glyceride containing the polyunsaturated fatty acid;

wherein the microorganism oil glyceride containing the polyunsaturated fatty acid is derived from *Mortierella* sp.;

wherein the hydrolysis by the lipase is performed in the presence of 10 to 200 weight percent of water based on a total weight of the microorganism oil glyceride containing the polyunsaturated fatty acid, and at a temperature from 10° C. to 20° C.;

wherein the lipase is derived from *Candida cylindracea*; and wherein saturated fatty acid content in the resulting glyceride is less than the saturated fatty acid content in the glyceride prior to the concentrating.

* * * * *